Figure 2:
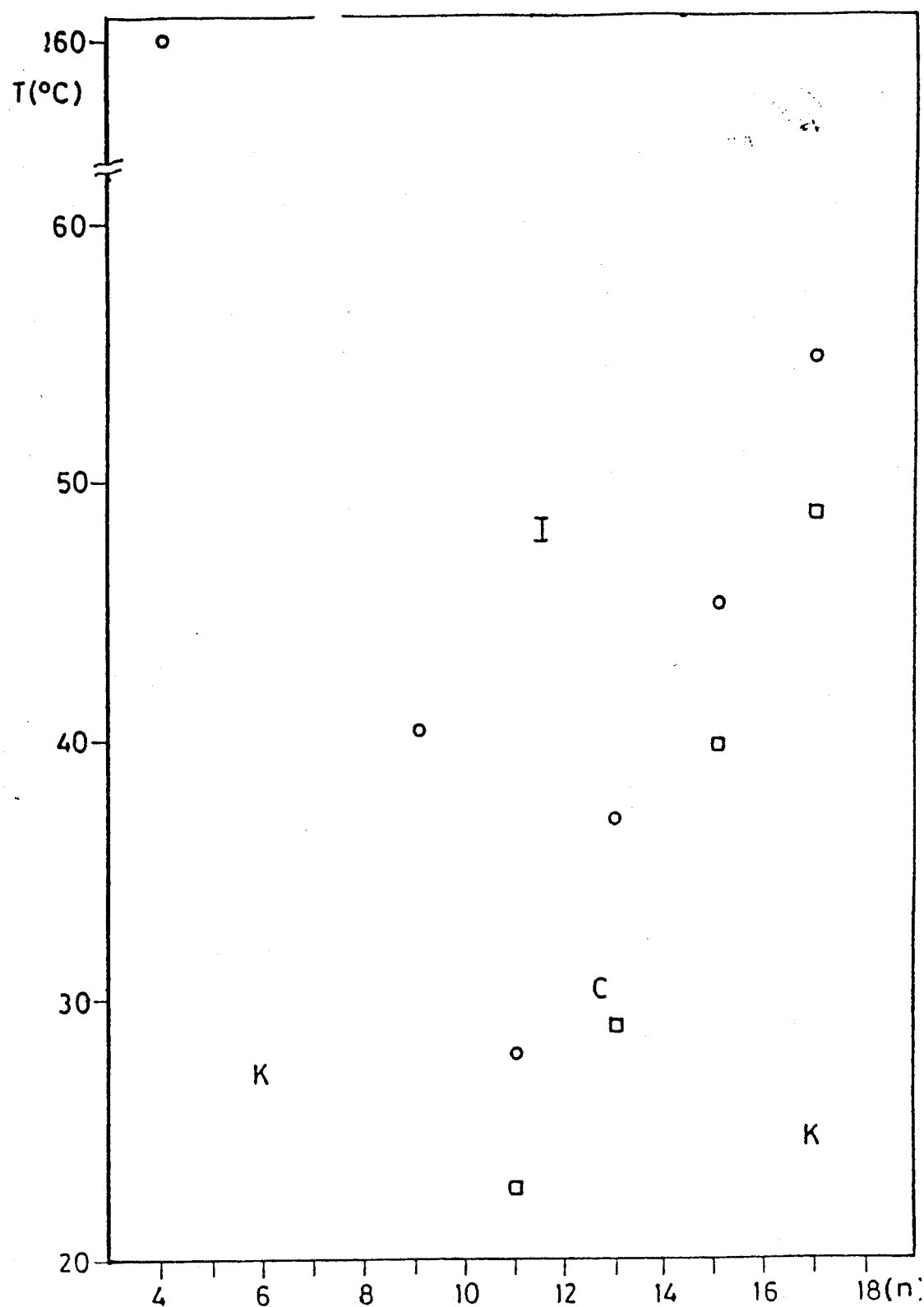

United States Patent [19]

Dal Canale et al.

[11] Patent Number: 4,918,217

[45] Date of Patent: Apr. 17, 1990

[54] MACROCYCLIC TETRAMERS HAVING COLUMNAR TRIDIMENSIONAL MESOPHASES

[75] Inventors: Enrico Dal Canale; Stefanio Bonsignore; Annick Du Vosel, all of Novara, Italy

[73] Assignee: Montedison S.p.A., Milan, Italy

[21] Appl. No.: 221,609

[22] Filed: Jul. 20, 1988

[30] Foreign Application Priority Data

Jul. 21, 1987 [IT] Italy .................................. 21370 A/87

[51] Int. Cl.$^4$ ........................ C07C 69/76; C09F 05/08
[52] U.S. Cl. .................................. 560/073; 260/410.5; 428/001; 350/330
[58] Field of Search ..................... 560/073; 260/410.5; 428/001; 350/330

[56] References Cited

PUBLICATIONS

Hoegberg, A. G., Sverker, J. Org. Chem. 45(22), 4498–500, 1980.

Primary Examiner—Paul J. Killos
Attorney, Agent, or Firm—Stevens, Davis, Miller & Mosher

[57] ABSTRACT

Octa-substituted derivatives of the macrocyclic tetramers obtained by condensation of resorcinol with an alkyl aldehyde, wherein the sutstituents are alkanoyl, p-alkylbenzoyl, and p-alkoxybenzoyl chains. These substituted tetramers show stable, tridimensional, columnar type mesophases wherein the crystalline lattice is formed with the central macrocyclic rings stacked one on another according to ordered columns, each ring being surrounded with alkyl chains in the melted state.

7 Claims, 2 Drawing Sheets

MACROCYCLIC TETRAMERS HAVING COLUMNAR TRIDIMENSIONAL MESOPHASES

DESCRIPTION OF THE INVENTION

The present invention relates to macrocyclic tetramers, which form stable, columnar, tridimensional mesophases.

By the term "columnar tridimensional mesophases", as used in the present specification and in the appended claims, a structure ordered in three dimensions is meant, wherein the molecules arrange themselves as columns.

This type of mesophase is described, e.g., in "Journal de Physique", 1985, 47, page 351.

U.S. Pat. No. 4,619,788 discloses hexa-substituted derivatives of tribenzo-cyclo-nona-tri-ene having a mesophase of the pyramidal type. These are molecules provided with a central rigid core having a pyramidal structure, wherein the substituent chains are symmetrically bonded to the base of the pyramid. These compounds have an electrical dipolar moment which makes them particularly suitable for being used as "memory devices", or as displays for opto-electronics device.

In accordance with the presdent invention it has now been discovered that octa-substituted derivatives of the macrocyclic tetramer obtained by condensing resorcinol with an alkyl aldehyde, wherein the substituents are alkanoyl, p-alkylbenzoyl and p-alkoxybenzoyl chains, are products which form stable, columnar, tridimensional mesophases.

Therefore the objects of the present invention are macrocyclic tetramers having stable columnar tridimensional mesophases of the formula:

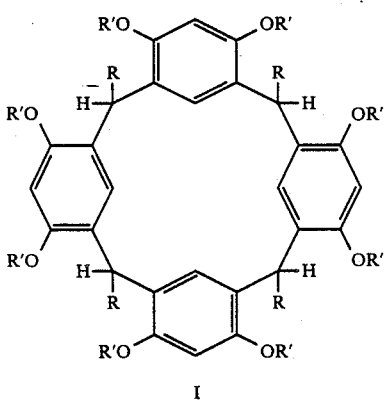

(I)

wherein:
R is an alkyl radical having from 1 to 3 carbon atoms, and
R', either equal to or different from one another, represents a radical selected from those having the formula:

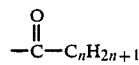

(II)

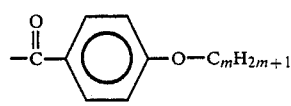

(III)

and

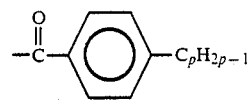

(IV)

wherein:
n is an integer higher than or equal to 10, and
m and p are integers higher than or equal to 11.

Among the tetramers having the formula (I), preferred are those wherein n is an integer within the range of from 11 to 25, and m and p are integers from 11 to 25.

The R' substituents of the same molecule may be equal to, or different from, one another; however, those compounds wherein R' radicals are equal to one another are preferred.

Figure 1:
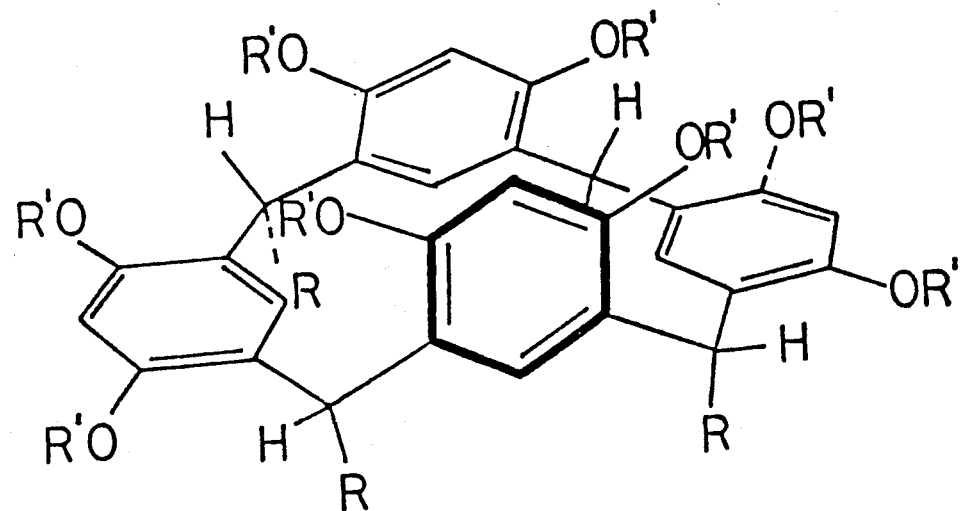

In the macrocyclic tetramers of the present invention, the R groups are positioned in an axial position, as shown in FIG. 1, which represents a perspective view of the molecule. This type of structure tends to form stable, tridimensional, columnar type mesophases wherein the crystalline lattice is formed with the central macrocyclic rings stacked one on another according to ordered columns, each ring being surrounded with alkyl chains in the melted state.

The tetramers having the formula (I) have melting temperatures within the range of from 0° to 150° C., and the tridimensional mesophase arrangement may be evidenced by analysis on a differential scanning calorimeter (DSC), analysis on an optical microscope under polarized light, and X-ray diffraction.

The temperatures at which the molten material turns into isotropic material (the clearing points) are generally within the range of from 20° to 250° C.

In FIG. 2, for exemplifying purposes, the temperatures of transition between the various phases are reported of a macrocyclic tetramer having the formula (I), wherein R is $CH_3$ and R' is the radical:

In said FIG. 2, the temperatures are reported on the ordinate while on the abscissa are reported the values of n; by I, C and K, the isotropic phase, the columnar tridimensional mesophase and the crystalline phase, respectively, are indicated.

In particular, in FIG. 2 the points marked by the small circles represent clearing points, and those marked by small squares represent the crystal-columnar mesophase transition.

The macrocyclic tetramers of the present invention show a dipolar moment different from zero, which makes them suitable for use in the opto-electronics field, or, more particularly, in the field of photonics as components for non-linear optical devices.

Moreover, they may be ferro-electric when the columns have the same direction of polarization and, therefore, they may be used as memory devices.

The macrocyclic tetramers of the present invention are prepared by reacting a macrocyclic tetramer having the formula:

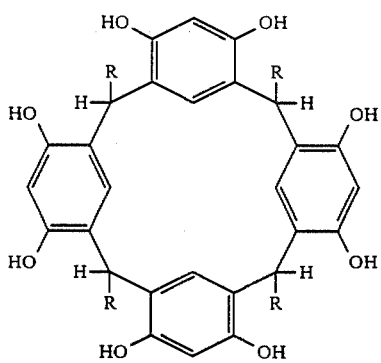

(V)

with alkanoyl halides of formula R'—X wherein X represents a halogen atom, preferably chlorine, and R' has the above meaning.

Examples of alkanoyl halides are lauroyl chloride, myristoyl chloride, palmitoyl chloride, stearoyl chloride, para-pentyl-benzoyl chloride, p-dodecyloxybenzoyl chloride, p-hexylbenzoyl chloride, p-hexadecanoyloxybenzoyl chloride, and so forth.

The reaction may be carried out as a normal solventless esterification under ambient pressure, and at a temperature within the range of from 50° to 200° C.

As an alternative, the reaction may be carried out in a solvent vehicle of a basic character, such as pyridine or tertiary amine; in this second case, the reaction temperature is preferably within the range of from 0° to 50° C.

The cyclic tetramers of formula (V) are per se known products, obtained by condensing resorcinol with alkyl aldehydes according to and as disclosed in "Journal of the American Chemical Society", 1932, 54, page 4325, and in "Journal of Organic Chemistry", 1980, 45, page 4498.

According to these processes, the products of formula (V) may be obtained as two configurational isomers, respectively, denominated the "boat isomer" and the "chair isomer", and separable by means of known techniques, e.g., by crystallization.

Only those compounds which are obtained by starting from the boat isomer, with all R groups thereof being in the axial position, form stable, tridimensional, columnar type mesophases.

In order still better to understand the present invention, some illustrative non-limiting examples thereof are now reported.

EXAMPLE 1

Preparation of 3.5.10.12.17.19.24.26-octadecanoyloxy-r-1c-8, c-15, c-22-tetramethyl-[14]-metacyclophane 0.545 g (1 mM) of tetramer having the formula (V) with R=CH$_3$, and 17.7 ml of palmitoyl chloride are heated for 6 hours at approximately 180° C. with stirring. When the reaction is ended, the excess chloride is distilled off under vacuum (120° C./5×10$^{-2}$ mm, Hg). The remaining residue is dissolved in CH$_2$Cl$_2$ and the resulting solution is first mixed and stirred with 0.1N NaOH, then washed with H$_2$O to neutral pH value, and finally thoroughly dried over sodium sulphate. The solvent is evaporated off, and the raw product is run twice through a silica gel column with 8/2 CH$_2$Cl$_2$/toluene and 8/2 CH$_2$Cl$_2$/hexane as eluents.

1.44 g of pure product is obtained (yield 59%).

Mass (DCI$^+$); MH$^+$ =2449.

NMR(CDCl$_3$): 0.89 ppm [t, 24H, J=6, 8 Hz, (CH$_2$)$_n$—CH$_3$]; 1.35 [bs, 192H, (CH$_2$)$_{12}$]; 1.45 (D, 12H, J=7, 4 Hz, CH—CH$_3$); 1.54 (m, 8H,

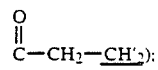

1.78 (m, 8H,

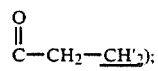

2.24 (m, 8H,

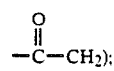

2.59 (m, 8H,

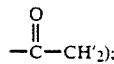

4.23 (q, 4H, J=7, 4 Hz, CH); 5.94 (s, 2H, Ar-H$_A$); 6.75 (s, 2H, AR-H$_B$); 6.90 (s, 2H, Ar-H'$_B$); 7.36 (s, 2H, Ar-H'$_A$).

Elemental analysis for C$_{160}$H$_{272}$O$_{16}$: theoretical: C=78.38%; H=11.18%. found: C=78.42%; H=11.28%.

EXAMPLES 2-3

By operating as in Example 1, but using respectively lauroyl chloride and stearoyl chloride, obtained were:

(3.5,10.12.17.19.24.26-octadodecanoyloxy-r-1,c-8,c-15, c-22-tetramethyl-[14]metacyclophane, with 60% yield after purification through a silica gel column with 7/3 CH$_2$Cl$_2$/toluene as the eluent.

Mass (DCI$^+$); MH$^+$ =2001.

NMR (CDCl$_3$): 0.88 ppm [t, 24H, J=6, 6 Hz, (CH$_2$)$_n$—CH$_3$]; 1.28 [bs, 128H, (CH$_2$)$_8$]; 1.44 (d, 12H, J=7, 2 Hz, CH—CH$_3$); 1.53 (m, 8H,

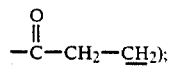

1.75 (m, 8H,

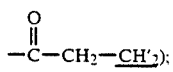

2.24 (m 8H,

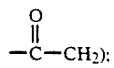

2.59 (m, 8H,

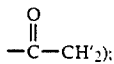

4.22 (q, 4H, J=7, 2 Hz, CH); 5.94 (s, 2H, Ar-H$_A$); 6.75 (s, 2H, Ar-H$_B$); 6.91 (s, 2H, Ar-H′$_B$); 7.36 (s, 2H, Ar-H′$_A$).

Elemental analysis for C$_{128}$H$_{208}$O$_{16}$: theoretical: C=76.75%; H=10.47%. found: C=76.44%; H=10.52%.

3.5.10.12.17.19.24.26-octaoctadecanoyloxy-r-1,c-8, c-15, c-22-tetramethyl-[1$_4$]metacyclophane, with 62% yield after double purification through a silica gel column with 7/3 CH$_2$Cl$_2$/hexane and 6/4 CH$_2$Cl$^2$/hexane as the eluents.

Mass (DCI+); MH+ =2673.

NMR(CDCl$_3$): 0.87 ppm [t, 24H, J=6, 7 Hz, (CH$_2$)$_n$—CH$_3$]; 1.28 [bs, 224H (CH$_2$)$_{14}$]; 1.43 (D, 12H, J=7, 5 Hz, CH—CH$_3$); 1.51 (m, 8H,

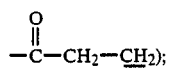

1.75 (m, 8H,

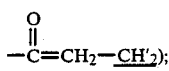

2.22 (m, 8H,

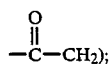

2.57 (m, 8H,

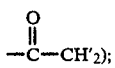

4.22 (q, 4H, J=7, 5 Hz, CH); 5.91 (s, 2H, Ar-H$_A$); 6.72 (s, 2H, Ar-H$_B$); 6.88 (s, 2H, Ar-H′$_B$); 7.38 (s, 2H, Ar-H′$_A$).

Elemental analysis for C$_{176}$H$_{304}$O$_{16}$: theoretical: C=78.98%; H=11.45%. found: C=78.80%; H=11.38%.

EXAMPLES 4-5 (COMPARATIVE EXAMPLES)

By operating as in Example 1, but using respectively hexanoyl chloride, and decanoyl chloride two products were obtained having no columnar mesophases, namely: 3.5.10.12.17.19.24.26-octahexanoyloxy-r-1,c-8,c-15,c-22-tetramethyl-[1$_4$]metacyclophane, with yield of 68%.

Elemental analysis for C$_{80}$H$_{112}$O$_{16}$: theoretical: C=72.26%; H=8.49%. found: C=72.25%; H=8.42%.

Mass (DCI+): MH+ =1329.

3.5.10.12.17.19.24.26-octadecanoyloxy-r-1, c-8,c-15, c-22-tetramethyl-[1$_4$]metacyclophane, with yield of 62%.

Elemental analysis for C$_{112}$H$_{176}$O$_{16}$: theoretical: 75.63%; H=9.97%. found: C=75.67%; H=10.05%.

Mass (DCI+): MH+ =1777.

EXAMPLE 6

By operating as in Example 1, using tetradecanoyl chloride, obtained is:

3.5.10.12.17.19.24.26-octatetradecanoyloxy-r-1,c-8, c-15,c-22-tetramethyl-[1$_4$]metacyclophane, with yield of 60%.

Elemental analysis for C$_{144}$H$_{240}$O$_{16}$: theoretical: C=77.65%; H=10.86%. found: C=77,57%; H=11.01%.

Mass (DCI+): MH+ =2225.

In the following Table 1, the transition temperatures and enthalpies of the products disclosed in Examples 1–6 are reported.

TABLE 1

Transition Temperatures (°C.), Enthalpies (kJ/mol. in brackets), of Octa-alkanoyl-Tetramers $$R' = -\overset{O}{\underset{\|}{C}}-C_nH_{2n+1}$$

| n | Yields | K | C | I |
|---|--------|---|---|---|
| 5 | 68% | . |  | 160.3 . |
|   |      |   |  | (41.8) |
| 9 | 62% | . |  | 40.3 . |
|   |      |   |  | (27.3) |
| 11 | 60% | . | 23.0 | 28.1 . |
|    |     |   | (12.5) | (27.3) |
| 13 | 60% | . | 28.9 | 37.0 . |
|    |     |   | (15.3) | (1.0) |
| 15 | 59% | . | 40.0 | 45.5 . |
|    |     |   | (53.0) | (48.2) |
| 17 | 62% | . | 49.0 | 55.0 . |
|    |     |   | (31.9) | (105.6) |

I = Isotropic phase
C = Tridimensional columnar mesophase
K = Crystalline phase
(.) = Observed phase

EXAMPLE 7

Preparation of 3.5.10.12.17.19.24.26-octa-p-dodecyloxybenzoyloxy-r-1,c-8, c-15, c-22-tetramethyl-[1$_4$]metacyclophane 0.545 g (1 mM) of tetramer of formula (V), with R=CH$_3$, and 5.2 g (16 mM) of p-dodecyloxybenzoyl chloride are heated for 8 hours at about 180° with stirring. When the reaction is ended the solid residue is dissolved in CH$_2$Cl$_2$ and the thus-obtained solution is mixed and stirred with NaOH (0.1N), then washed with water to a neutral pH and finally dried through sodium sulphate. The residue after evaporation is chromatographed twice over silica gel with CH$_2$Cl$_2$ as the first eluent, and CHCl$_3$ as the second eluent. 1.17 g of pure product are obtained; yield 41%.

Mass (DCI+); MH+ =2849.

NMR(CDCl$_3$): 0.87 ppm [t, 24H, J=6, 6 Hz, (CH$_2$)$_n$—CH$_3$]; 1.26 [bs, 128H, (CH$_2$[$_8$]; 1.44 (m, 16H, O—CH—CH$_2$—CH$_2$); 1.58 (d, 12H, J=6, 8 Hz, CH—CH$_3$); 1.79 (m, 16H, O—CH—CH$_2$—CH$_2$); 3.93 (m, 8H, O—CH$_2$); 4.01 (t, 8H, J=6, 1 Hz, O—CH′$_2$); 4.61 (q, 4H, J=6, 8 Hz, CH); 6.38 (s, 2H, Ar-H$_A$); 6.73 (d, 8H, J=8, 7 Hz, Ar-H$_1$); 6.83 (d, 8H, J=8, 7 Hz, Ar-H′$_1$); 7.06 (s, 2H, Ar-H′$_B$); 7.20 (s, 2H, Ar-H′$_B$); 7.60 (s, 2H, Ar-H′$_A$); 7.72 (d, 8H, J=8, 7 Hz, Ar-H$_2$); 7.76 (d, 8H, J=8, 7 Hz, Ar-H′$_2$).

Elemental analysis for C$_{84}$H$_{256}$O$_{24}$: theoretical: C=77.49%; H=9.05%.

EXAMPLE 8

By operating as in Example 7, using p-hexadecyloxybenzoylchloride, there is obtained, after purification through a silica gel column with 85/15 CH$_2$Cl$_2$/hexane as the eluent, the compound 3.5.10.12.17.19.24.26-octa-p-hexadecyloxybenzoyloxy-r-1, c-8, c-15, c-22-tetramethyl-[1$_4$]metacyclophane with yield of 44%.

Elemental analysis for C$_{216}$H$_{320}$O$_{24}$: theoretical: C=78.59%; H=9.77%. found: C=78.67%; H=9.77%.

Mass (DCI+): MH+ =3297.

TABLE 2

Transition temperatures (°C.), Enthalpy (KJ/mol in parentheses) of octa-p-alkyloxybenzoyloxy-tetramer:

$$R' = -\overset{O}{\underset{\|}{C}} - \bigcirc - O - C_mH_{2m-1}$$

| m | Yields | K | C | I |
|---|--------|---|---|---|
| 12 | 41% | . | 3.0 | . | 111.0 | . |
| | | | (32.1) | | (36.3) | |
| 16 | 44% | . | 43.0 | . | 106.5 | . |
| | | | (124.0) | | (53.8) | |

What is claimed is:

1. Macrocylic tetramers, having stable, columnar, tridimensional mesophases, having the formula:

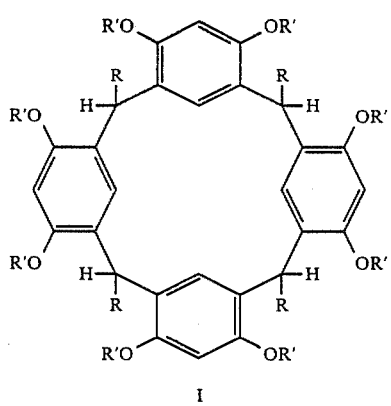

(I)

wherein:
R is an alkyl radical having from 1 to 3 carbon atoms, and
R', either equal to or different from one another, represents a radical selected from those having the formula:

$$-\overset{O}{\underset{\|}{C}} - C_nH_{2n+1}$$ (II)

$$-\overset{O}{\underset{\|}{C}} - \bigcirc - O - C_mH_{2m+1}$$ (III)

$$-\overset{O}{\underset{\|}{C}} - \bigcirc - C_pH_{2p+1}$$ (IV)

wherein:
n is an integer higher than or equal to 10, and
m and p are integers higher than or equal to 11.

2. A tetramer according to claim 1, wherein n is an integer of from 11 to 25, and m and p are integers of from 11 to 25.

3. A tetramer according to claim 1 or 2, wherein the R' radicals are equal to one another.

4. A tetramer according to claim 1 or 2, having a melting point within the range of from 0° to 150° C.

5. A tetramer according to claim 1 or 2, wherein the tridimensional mesophase is of the columnar type.

6. A memory device, an opto-electronic display, or a non-linear optical device having as a component a macrocyclic tetramer having stable, columnar, tridimensional mesophases, having the formula:

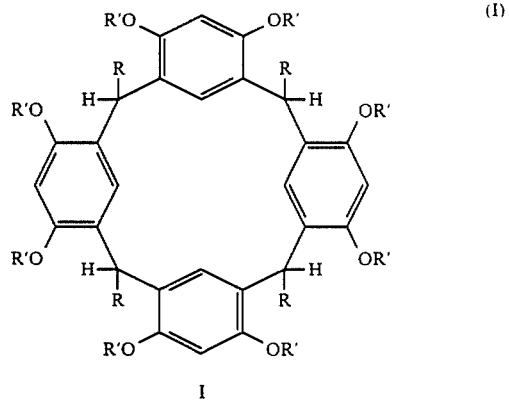

(I)

wherein:
R is an alkyl radical having from 1 to 3 carbon atoms, and R', either equal to or different from one another, represents a radical selected from the those having the formula:

(II)

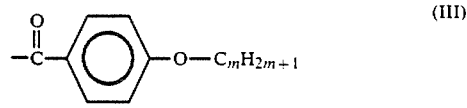

(III)

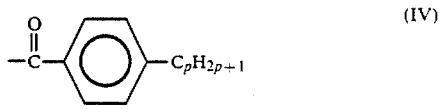

(IV)

wherein:
n is an integer higher than or equal to 10, and m and p are integers higher than or equal to 11.

7. A memory device, an opto-electronic display, or a non-linear optical device having as a component a macrocyclic tetramer having stable, columnar, tridimensional mesophases, having the formula:

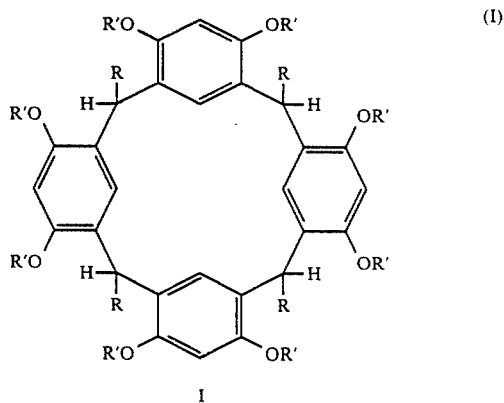

(I)

wherein:

R is an alkyl radical having from 1 to 3 carbon atoms, and R', either equal to or different from one another, represents a radical selected from the those having the formula:
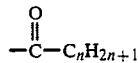 (II)
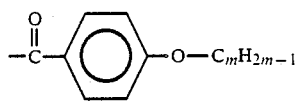 (III)
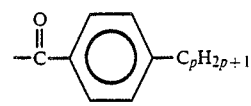 (IV)
wherein:
n is an integer of from 11 to 25, and m and p are integers of from 11 to 25.
* * * * *